(12) United States Patent
Wegener et al.

(10) Patent No.: US 11,191,879 B2
(45) Date of Patent: Dec. 7, 2021

(54) CELL PROCESSING SYSTEM AND METHOD WITH PRELIMINARY PROCESS EVALUATION

(71) Applicant: Fenwal, Inc., Lake Zurich, IL (US)

(72) Inventors: Christopher J. Wegener, Libertyville, IL (US); Daniel Boggs, Libertyville, IL (US); Bret M. Olson, Chicago, IL (US); Steven C. Binninger, Evanston, IL (US); James D. Hosek, Westchester, IL (US)

(73) Assignee: FENWAL, INC., Lake Zurich, IL (US)

( * ) Notice: Subject to any disclaimer, the term of this patent is extended or adjusted under 35 U.S.C. 154(b) by 0 days.

(21) Appl. No.: 15/456,853

(22) Filed: Mar. 13, 2017

(65) Prior Publication Data
US 2017/0340783 A1 Nov. 30, 2017

Related U.S. Application Data

(60) Provisional application No. 62/342,675, filed on May 27, 2016.

(51) Int. Cl.
*A61M 1/00* (2006.01)
*A61M 1/02* (2006.01)
(Continued)

(52) U.S. Cl.
CPC ............ *A61M 1/00* (2013.01); *A61M 1/0272* (2013.01); *A61M 1/262* (2014.02); *A61M 1/265* (2014.02);
(Continued)

(58) Field of Classification Search
CPC ...... A61M 1/00; A61M 1/0272; A61M 1/262; A61M 1/265; A61M 1/34; A61M 1/3692;
(Continued)

(56) References Cited

U.S. PATENT DOCUMENTS 3,877,634 A 4/1975 Rohde et al.
4,835,372 A 5/1989 Gombrich et al.
(Continued)

FOREIGN PATENT DOCUMENTS

DE 20305506 1/2004
EP 2745864 6/2014
(Continued)

OTHER PUBLICATIONS

Fresenius Kabi, Lovo Cell processing system, Filtration Technology Designed for Labs Like Yours. (2014).
(Continued)

*Primary Examiner* — Pranav N Patel
(74) *Attorney, Agent, or Firm* — Cook Alex Ltd.

(57) ABSTRACT

A cell processing system includes a processor connectable to a source container filled with a biological fluid, the processor including a separator configured to separate the biological fluid from the source container into at least two streams according to a process including at least one process parameter, and a controller coupled to the processor and an input. The controller is configured to receive the at least one process parameter, to evaluate the process using the at least one process parameter before performing the process, and to carry out one or more actions based on the evaluation, such as providing an output estimate to the operator, preventing the process from being performed according to a comparison between a calculated condition and a control, or providing an error indication to the operator according to the calculated condition and a measured in-process condition.

21 Claims, 7 Drawing Sheets

(51) Int. Cl.
*A61M 1/34* (2006.01)
*G16H 10/40* (2018.01)
*A61M 1/26* (2006.01)
*A61M 1/36* (2006.01)

(52) U.S. Cl.
CPC ............ *A61M 1/34* (2013.01); *A61M 1/3692* (2014.02); *A61M 1/3693* (2013.01); *G16H 10/40* (2018.01); *A61M 2205/75* (2013.01)

(58) Field of Classification Search
CPC .. A61M 1/3693; A61M 2205/75; G16H 10/40
See application file for complete search history.

(56) References Cited

U.S. PATENT DOCUMENTS

| | | | |
|---|---|---|---|
| 5,053,121 | A | 10/1991 | Schoendorfer et al. |
| 5,194,145 | A | 3/1993 | Schoendorfer |
| 5,240,856 | A | 8/1993 | Goffe et al. |
| 5,458,566 | A | 10/1995 | Herrig et al. |
| 5,536,475 | A | 7/1996 | Moubayed et al. |
| 5,573,678 | A | 11/1996 | Brown et al. |
| 5,769,811 | A | 6/1998 | Stacey et al. |
| 5,865,718 | A | 2/1999 | Chan |
| 5,956,023 | A | 9/1999 | Lyle et al. |
| 6,060,022 | A | 5/2000 | Pang et al. |
| 6,175,420 | B1 | 1/2001 | Barry et al. |
| 6,284,142 | B1 | 9/2001 | Muller |
| 6,325,775 | B1 | 12/2001 | Thom et al. |
| 6,466,879 | B1 | 10/2002 | Cantu et al. |
| 6,605,223 | B2 | 8/2003 | Jorgensen et al. |
| 6,622,052 | B1 | 9/2003 | Rosiello |
| 6,716,151 | B2 | 4/2004 | Panzani et al. |
| 6,730,054 | B2 | 5/2004 | Pierce et al. |
| 6,736,788 | B1 | 5/2004 | Mongomery et al. |
| 7,044,927 | B2 | 5/2006 | Mueller et al. |
| 7,072,769 | B2 | 7/2006 | Fletcher-Haynes et al. |
| 7,363,167 | B2 | 4/2008 | Csore et al. |
| 7,390,484 | B2 | 6/2008 | Fraser et al. |
| 7,430,478 | B2 | 9/2008 | Fletcher-Haynes et al. |
| 7,651,474 | B2 | 1/2010 | Van Waeg et al. |
| 7,963,901 | B2 | 6/2011 | Langley et al. |
| 8,150,548 | B2 | 4/2012 | Raghibizadeh et al. |
| 8,357,298 | B2 | 1/2013 | Demers et al. |
| 8,415,145 | B2 | 4/2013 | Fukuda et al. |
| 8,539,573 | B2 | 9/2013 | Newlin et al. |
| 8,883,499 | B2 | 11/2014 | Hedrick et al. |
| 8,900,172 | B2 | 12/2014 | Pohlmeier |
| 8,905,959 | B2 | 12/2014 | Basaglia |
| 8,945,376 | B1 | 2/2015 | Cordisco |
| 2002/0179544 | A1 | 12/2002 | Johnson et al. |
| 2003/0018289 | A1 | 1/2003 | Ng et al. |
| 2003/0069480 | A1 | 4/2003 | Ng et al. |
| 2003/0199379 | A1 | 10/2003 | Schneider et al. |
| 2004/0248077 | A1 | 12/2004 | Rodriguez Rilo et al. |
| 2005/0070837 | A1 | 3/2005 | Ferrarini et al. |
| 2005/0215937 | A1 | 9/2005 | Spinale et al. |
| 2007/0219826 | A1 | 9/2007 | Brodsky et al. |
| 2008/0040153 | A1 | 2/2008 | Davis, Jr. |
| 2009/0191174 | A1 | 7/2009 | Boudreau et al. |
| 2009/0211987 | A1 | 8/2009 | Min |
| 2011/0045959 | A1 | 2/2011 | Kurihara et al. |
| 2011/0206643 | A1 | 8/2011 | Fulga et al. |
| 2011/0244443 | A1 | 10/2011 | van Rijn et al. |
| 2013/0092630 | A1 | 4/2013 | Wegener |
| 2013/0267884 | A1 | 10/2013 | Boggs et al. |
| 2013/0299399 | A1 | 11/2013 | Suffritti et al. |
| 2013/0334139 | A1* | 12/2013 | Blickhan ............ A61M 1/3496 210/650 |
| 2014/0081193 | A1 | 3/2014 | Watters et al. |
| 2014/0234183 | A1 | 8/2014 | Kolenbrander et al. |
| 2014/0266983 | A1 | 9/2014 | Christensen |
| 2014/0282181 | A1 | 9/2014 | Declerck |
| 2014/0291248 | A1* | 10/2014 | Foley .................. A61M 1/3693 210/662 |
| 2017/0262601 | A1 | 9/2017 | Binninger et al. |
| 2018/0015418 | A1 | 1/2018 | Binninger et al. |

FOREIGN PATENT DOCUMENTS

| | | |
|---|---|---|
| WO | WO81/02979 | 10/1981 |
| WO | WO00/20053 | 4/2000 |
| WO | WO02/062484 | 8/2002 |
| WO | WO02/069793 | 9/2002 |
| WO | WO02/088897 | 11/2002 |
| WO | WO02/089340 | 11/2002 |
| WO | WO2004/032999 | 4/2004 |
| WO | WO2009/072510 | 6/2009 |
| WO | WO2012/021167 | 2/2012 |
| WO | WO2012/125457 | 9/2012 |
| WO | WO2012/125470 | 9/2012 |
| WO | WO2013/043433 | 3/2013 |

OTHER PUBLICATIONS

Fresenius Kabi, Lovo Cell Processing System, Choose filtered. (2014).

European Patent Office, extended European Search Report, counterpart EP Appl. No. 17160556.1, dated Oct. 19, 2017 (10 pages).

* cited by examiner

CELL PROCESSING SYSTEM AND METHOD WITH PRELIMINARY PROCESS EVALUATION

CROSS-REFERENCE TO RELATED APPLICATIONS

This application claims the benefit of U.S. Provisional Application No. 62/342,675, filed May 27, 2016, which is hereby incorporated herein by reference.

TECHNICAL FIELD

The present disclosure is generally directed to systems and methods for evaluating a procedure or process, or parts or portions thereof, prior to the process being performed, and to biological fluid processing systems and methods employing such. More particularly, the present disclosure is directed to the controlled processing of biological fluid using a disposable fluid circuit and a reusable processing machine, where the processing is evaluated before it is performed.

BACKGROUND

The processing of biological fluid such as blood or blood components typically involves using a reusable processing machine ("hardware") and a disposable fluid circuit adapted for mounting or other association with the reusable apparatus. The fluid circuit typically includes (plastic) bags and associated tubing that defines a flow path through the circuit. The disposable fluid circuit may also include one or more separation devices where the biological fluid/cells can be separated into two or more components, washed or otherwise processed. Separation devices may separate the biological fluid based on centrifugal separation and/or, as described below, membrane separation.

Conventionally, assumptions are made regarding the operation of the apparatus, for example, concerning the time required to perform a procedure and the amount of fluid generated as waste as a consequence. Often, these assumptions are based on empirical data derived under conditions similar to, but not identical to, the conditions under which the biological fluid will be processed presently. As such, the operator is left to adjust his or her assumptions based on his or her experience with the apparatus and the process being performed. This can prove problematic where little or no empirical data exists on which the operator can base his or her assumptions, or where the operator has only limited experience with the apparatus, the process being performed, or the empirical data.

SUMMARY

In one aspect, a cell processing system includes a processor connectable to a source container filled with a biological fluid, the processor including a separator configured to separate the biological fluid from the source container into at least two streams according to a process including at least one process parameter, and a controller coupled to the processor and an input. The controller is configured to receive the at least one process parameter via the input, to calculate at least one output based on the at least one process parameter, and to provide the at least one calculated output to an operator prior to causing the processor to operate according to the process.

In another aspect, a method for evaluating a process is provided, the process to be performed using a processor connectable to a source container filled with a biological fluid, the processor including a separator configured to separate the biological fluid from the source container into at least two streams. The method includes receiving at least one process parameter to be used during the process, calculating at least one output based on the at least one process parameter, and providing the at least one calculated output to an operator prior to operating the processor according to the process.

In a further aspect, a cell processing system includes a processor connectable to a source container filled with a biological fluid, the processor including a separator configured to separate the biological fluid from the source container into at least two streams according to a process including at least one process parameter, and a controller coupled to the processor and an input. The controller is configured to receive the at least one process parameter via the input, to calculate at least one in-process condition based on the at least one process parameter, to compare the at least one calculated in-process condition with at least one in-process condition control, and to provide an error indication to an operator if the at least one calculated in-process condition does not match the at least one in-process condition control prior to causing the processor to operate according to the process.

In another aspect, a method for evaluating a process is provided, the process to be performed using a processor connectable to a source container filled with a biological fluid, the processor including a separator configured to separate the biological fluid from the source container into at least two streams. The method includes receiving at least one process parameter to be used during the process, calculating at least one in-process condition based on the at least one process parameter, comparing the at least one calculated in-process condition with at least one in-process condition control, and providing an error indication to an operator if the at least one calculated in-process condition does not match the at least one in-process condition control prior to operating the processor according to the process.

In yet another aspect, a cell processing system includes a processor connectable to a source container filled with a biological fluid, the processor including a separator configured to separate the biological fluid from the source container into at least two streams according to a process including at least one process parameter, and a controller coupled to the processor and an input. The controller is configured to receive the at least one process parameter via the input, to calculate at least one in-process condition based on the at least one process parameter prior to causing the processor to operate according to the process, to subsequently cause the processor to operate according to the process, to measure at least one in-process condition during operation of the processor, to compare the at least one calculated in-process condition with at least one measured in-process condition, and to provide an error indication to an operator if the at least one measured in-process condition does not match the at least one calculated in-process condition.

In a still further aspect, a method for evaluating a process is provided, the process to be performed using a processor connectable to a source container filled with a biological fluid, the processor including a separator configured to separate the biological fluid from the source container into at least two streams. The method includes receiving at least one process parameter to be used during the process, calculating at least one in-process condition based on the at least one process parameter prior to operating the processor according to the process, causing subsequently the processor to operate according to the process, measuring at least one in-process condition during operation of the processor, comparing the at least one calculated in-process condition with the at least one measured in-process condition, and providing an error indication to an operator if the at least one measured in-process condition does not match the at least one calculated in-process condition.

BRIEF DESCRIPTION OF THE FIGURES

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

DETAILED DESCRIPTION

Figure 1:
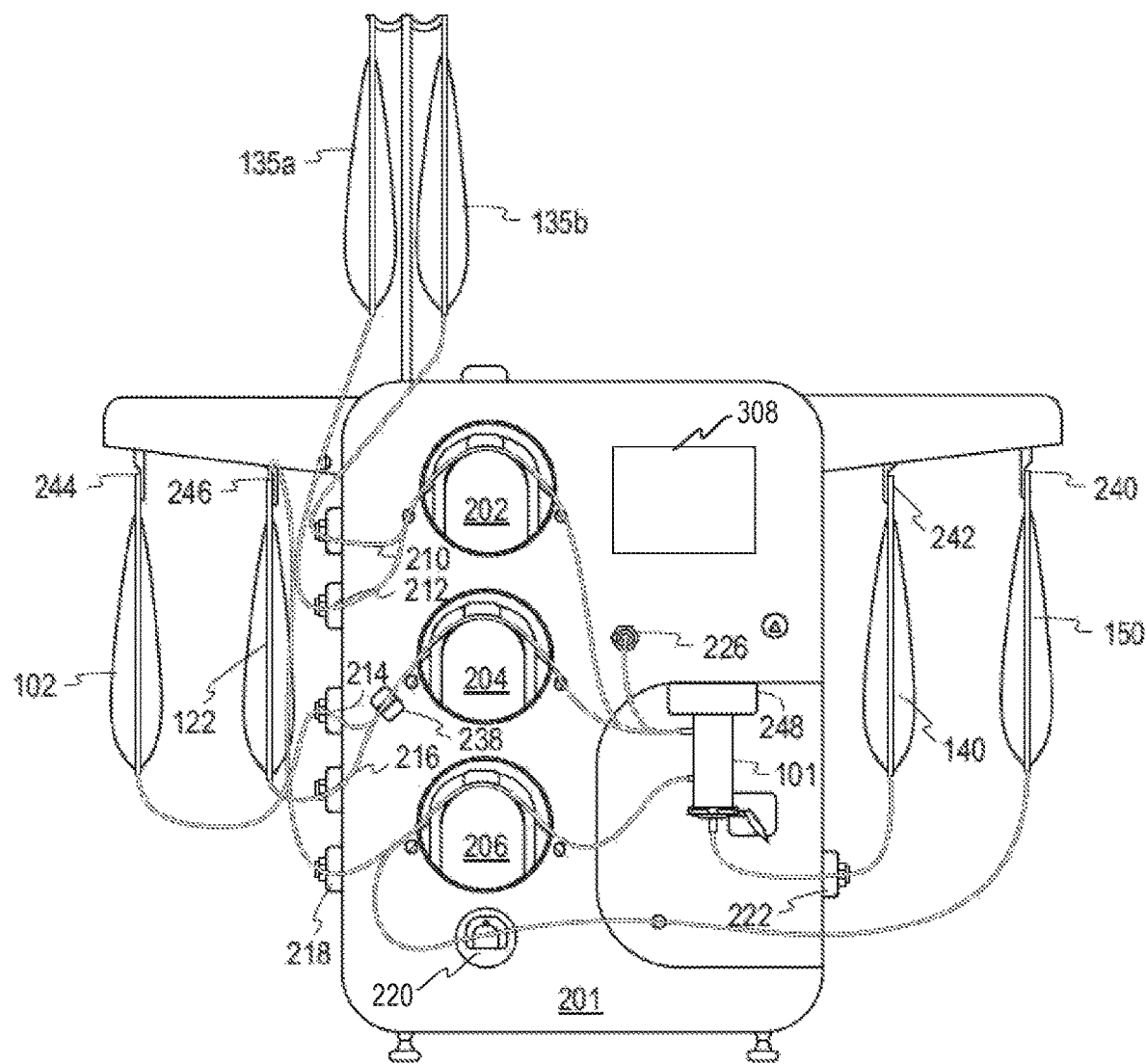
FIG. 1 is a frontal view of a reusable cell processing apparatus with a disposable fluid circuit loaded thereon.
Figure 2:
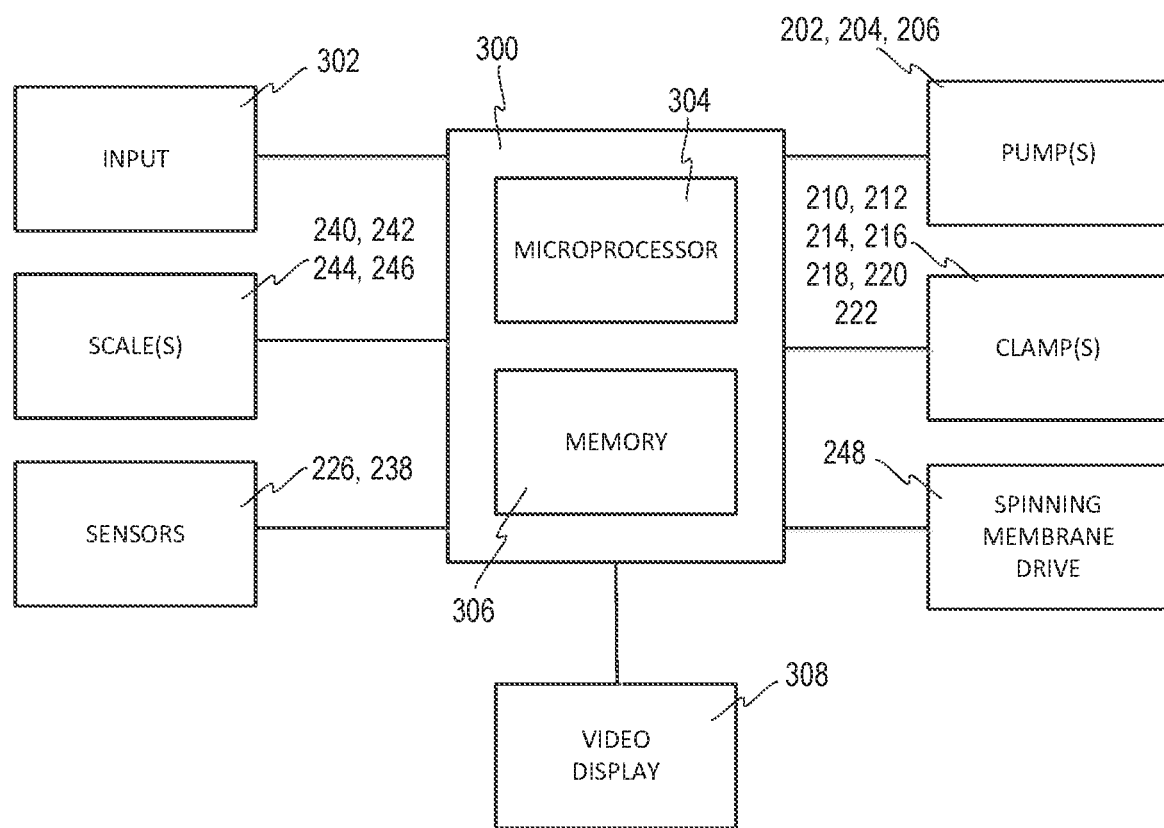
FIG. 2 is a schematic view of the control circuitry of the apparatus of FIG. 1.

As illustrated in FIGS. 1 and 2, a cell processing system includes a processor 100, 200 to receive a biological fluid to be processed, a control unit (or controller) 300 coupled to the processor, the controller 300 configured to operate the processor 100, 200 according to a procedure or process. The controller 300 is also configured to evaluate the process, or parts or portions thereof, prior to operating the processor 100, 200 according to the process. In particular, the controller may perform a pre-process calculation of one or more outputs (e.g., time to conduct the process, or parts or portions thereof, volume of wash media consumed, volume of waste fluid generated, volume of residuals remaining in final product, etc.) and/or one or more in-process conditions. The calculation may involve a mathematical model of the entire process, from initiation to completion. The calculated outputs and/or in-process conditions may be provided or displayed to the operator so that the operator may compare them against the operator's existing assumptions or to provide the operator with estimates that can be used on a going-forward basis. These outputs and/or in-process conditions may be compared with control values to warn the operator, prior to performing the process, that the process might exceed the abilities or physical constraints on the processor 100, 200 if performed. Further, the outputs and/or in-process conditions may be compared with values measured during operation of the processor 100, 200 to warn the operator that the process, as performed, is generating outputs or in-process conditions that differ from those expected, pre-process.

As explained in detail below, the processor 100, 200 may include a disposable fluid circuit 100 (see also FIGS. 3 and 5) and reusable hardware 200 (see also FIG. 4). According to the illustrated embodiments, the disposable fluid circuit 100 may include a spinning membrane 101, at least one container 102, 122, 135a, 135b, 140, 150 (of which at least containers 102, 135a, 135b may be initially separate and then connected to the remainder of the circuit 100 at the time of processing), and tubing 106, 120, 128, 132a, 132b, 162, 166, 168 connecting the spinning membrane 101 and the one or more containers 102, 122, 135a, 135b, 140, 150. As is also illustrated, the reusable hardware 200 may include at least one drive 248 to spin the spinning membrane 101, at least one scale 240, 242, 244, 246 to weigh the at least container 102, 122, 140, 150 and contents thereof, and at least one pump 202, 204, 206 to receive the tubing 162, 166, 168 and pump fluid therethrough such as by peristaltic action, although other types of pumps and pumping action may be used.

The controller 300 may, according to the embodiments, include a programmable microprocessor 304, which microprocessor 304 may be coupled to the at least one input 302 and may be programmed to operate the processor according to a process. In particular, the controller may be programmed to carry out a pre-process evaluation, resulting in the calculation of one or more outputs and/or one or more in-process conditions. As mentioned above, these outputs (and/or in-process conditions) may be provided to the operator, pre-process, for comparison against the operator's existing assumptions, for example. These outputs and/or in-process conditions may be compared with control values, pre-process, or values measured during operation of the processor, to provide warnings or error indications to the operator or limit or prevent the operation of the processor according to the process.

In addition, the embodiments illustrate a method of operating a cell processing system, the cell processing system including a processor 100, 200 to receive a biological fluid to be processed. The method may include a pre-process evaluation, resulting in the calculation of one or more outputs and/or one or more in-process conditions. These outputs (and/or in-process conditions) may be provided to the operator, pre-process, for comparison against the operator's existing assumptions, for example. Alternatively, these outputs and/or in-process conditions may be compared with control values, pre-process, or values measured during operation of the processor, to provide warnings or error indications to the operator to limit or prevent the operation of the processor according to the process.

An embodiment of the afore-mentioned system and method thus may provide one or more of the following advantages. Initially, the system and method may provide estimates for outputs that are uniform, considering that the controller is providing the estimates based on a uniform evaluation method and system. Moreover, the system and method may prevent operation of the processor in a manner that will damage the source material, create unsafe operating conditions, and/or produce a final product that does not meet the desired specifications. Further, the system and method may control the operation of the processor in a manner that will limit damage to the processor, the product, or both. In addition, the system and method may alert the operator to conditions during the operation that have deviated from the expected conditions, and that might require user intervention (e.g., the attachment of additional wash media containers or containers with greater capacity) to prevent interruption of processing. Other advantages may also result.

While the foregoing discussion references an embodiment in the form of a cell processing system, other systems may incorporate this technology as well. These systems may share the technical challenges faced by the aforementioned cell processing system, and incorporation of the technology may provide similar advantages.

For example, a separation system, more particularly a filtration system, or even more particularly a microfiltration system, also may include a processor to receive a fluid to be processed and a controller. Further, certain embodiments of such a processor may include a disposable fluid circuit (which circuit may include a membrane used for filtration) and reusable hardware, and the controller may be configured to operate the processor. According to such a system, the controller may be configured to evaluate the process, or parts or portions thereof, prior to operating the processor according to the process. This evaluation may include performing a pre-process calculation of a mathematical model of the entire process, from initiation to completion. The evaluation may also result in calculated outputs and/or in-process conditions, which may be provided to the operator or which may be used to generate automated warnings before or during the process that are provided to the operator.

Having thus described the system and method in general terms, the details of the system and method are described in detail.

As mentioned above, the systems disclosed herein typically include a reusable separation apparatus and one or more disposable processing circuits adapted for association with the reusable apparatus, which apparatus and circuit(s) define the processor. The reusable separation apparatus may be any apparatus that can provide for the automated processing of biological fluid. "Biological fluid" includes without limitation blood and blood components, and "cell" or "biological cell" includes without limitation blood cells, such as red cells, white cells and platelets. By "automated," it is meant that the apparatus can be programmed to carry out the processing steps of a biological fluid processing method without substantial operator involvement. Of course, even in the automated system of the present disclosure, it will be understood that operator activity may be involved, including the loading of the disposable fluid circuits and entering processing parameters. Additional manual steps may be required as well. However, the reusable apparatus can process biological fluid through the disposable circuit(s) described below without substantial operator intervention.

Figure 6:
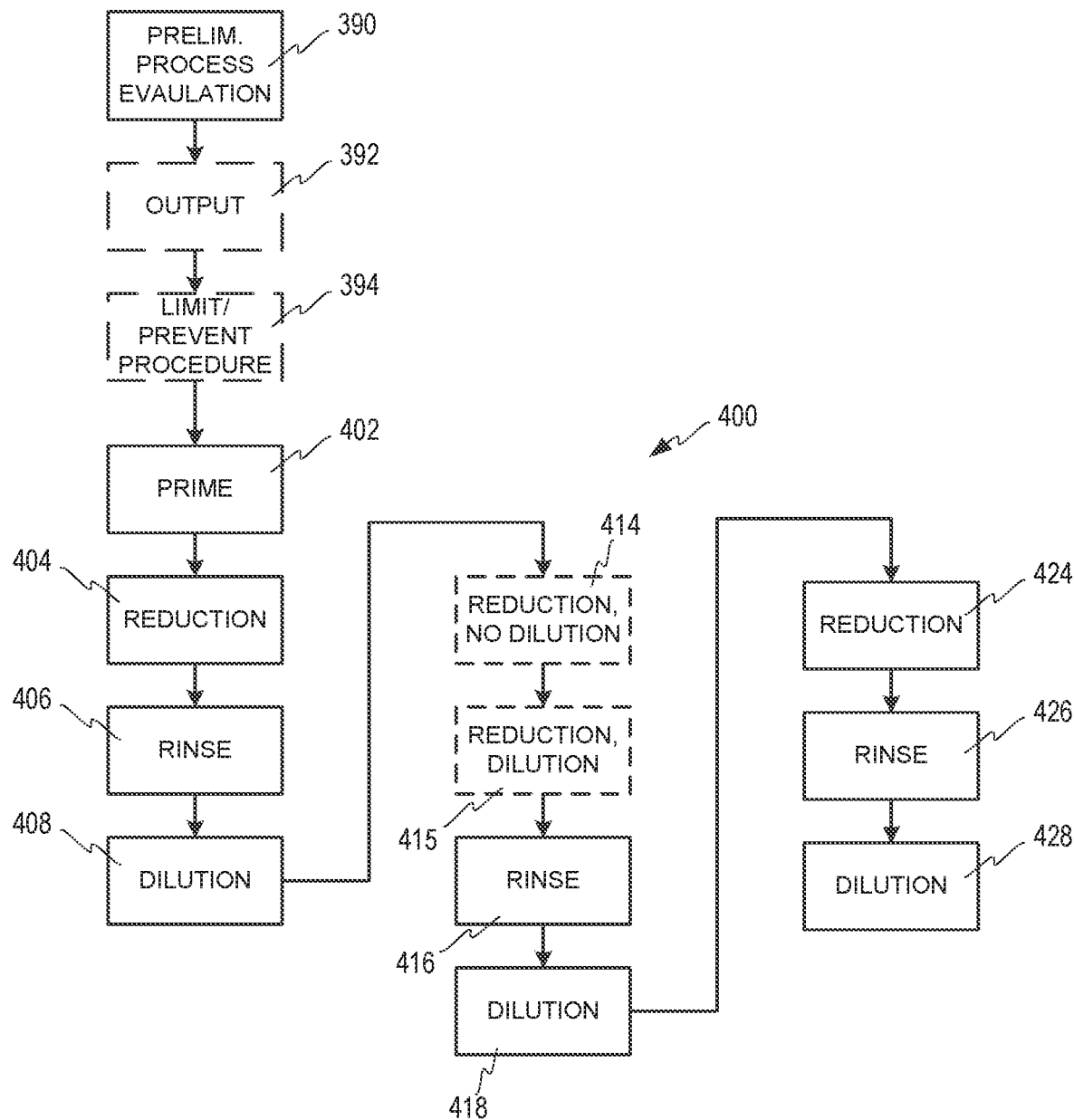
FIG. 6 is a flowchart of one embodiment of a method of operating a reusable cell processing apparatus with a disposable fluid circuit loaded thereon, such as is illustrated in FIG. 1, to process a biological fluid.
Figure 7:
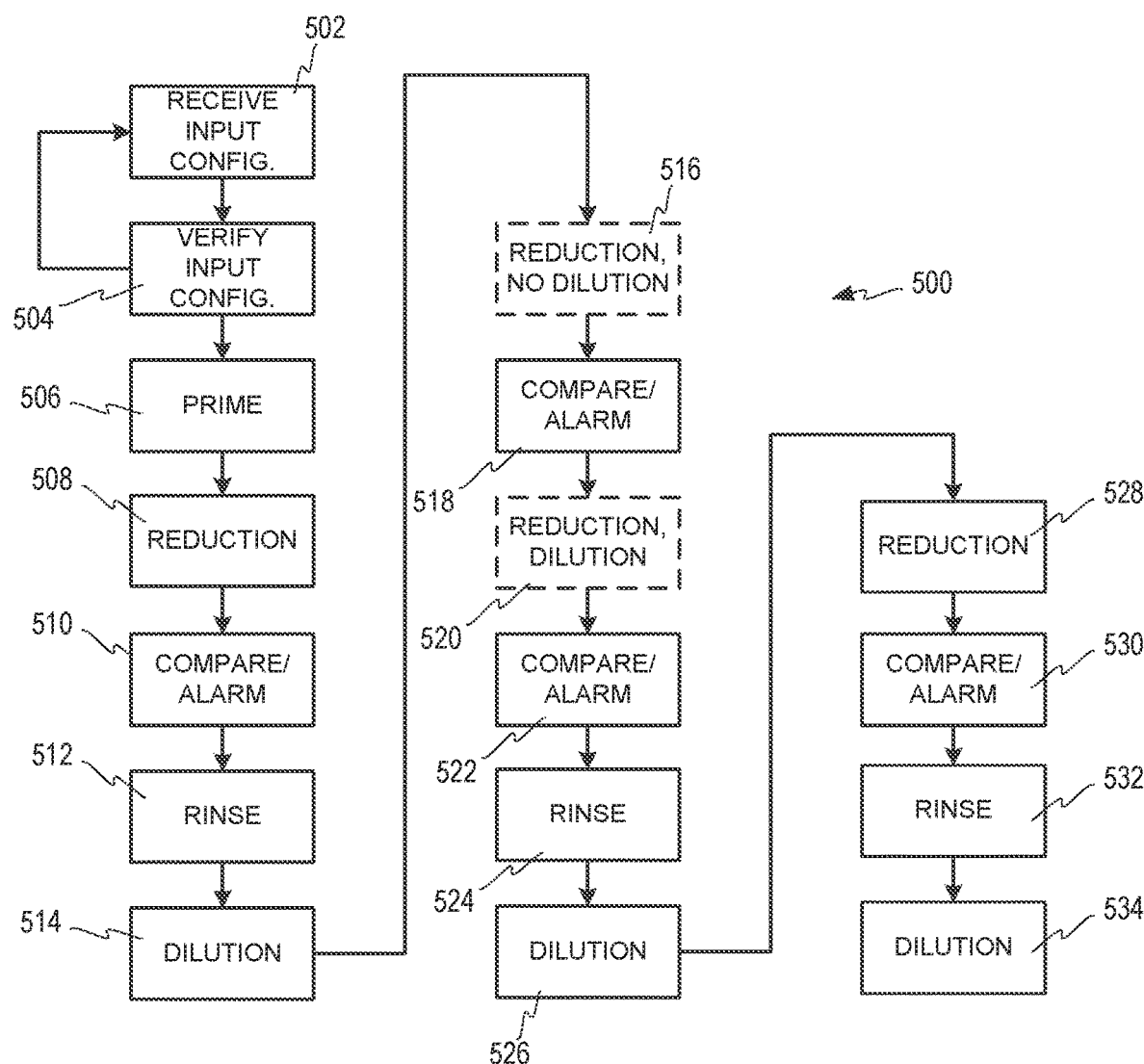
FIG. 7 is a flowchart of one embodiment of a method for evaluating a procedure, or a portion thereof, to be performed on, for example, a reusable cell processing apparatus with a disposable fluid circuit prior to the procedure being performed using the apparatus and fluid circuit.

The illustrated processing apparatus is typically capable of effecting the separation of a biological fluid that includes biological cells into two or more components or fractions. Thus, the reusable apparatus may generate conditions that allow for the separation of a biological fluid into selected components or fractions. One preferred machine for separating biological fluid into its constituent components or fractions uses a spinning porous membrane. An example of such machine is the Autopheresis C® sold by Fenwal, Inc. of Lake Zurich, Ill., which is an affiliate of Fresenius Kabi AG of Bad Homburg, Germany. A detailed description of a spinning membrane may be found in U.S. Pat. No. 5,194,145 to Schoendorfer, which is incorporated by reference herein in its entirety, and in International Application Publication No. WO 2012/125457, filed Mar. 9, 2012, the contents of which are also incorporated herein in their entirety. In addition, systems and methods that utilize a spinning porous membrane are also disclosed in U.S. Provisional Patent Application No. 61/537,856, filed on Sep. 22, 2011, and International Publication Application No. WO 2012/125470, filed Mar. 9, 2012, the contents of each are incorporated herein by reference. The references identified above describe a membrane-covered spinner having an interior collection system disposed within a stationary shell. While a detailed discussion of the separation device is beyond the scope of this application, the spinning membrane separation device is shown in FIGS. 6, 7(*a*)-7(*b*) of the reference cited and is discussed below in general terms. In another embodiment, the reusable apparatus may generate a centrifugal field to effect separation.

Figure 3:
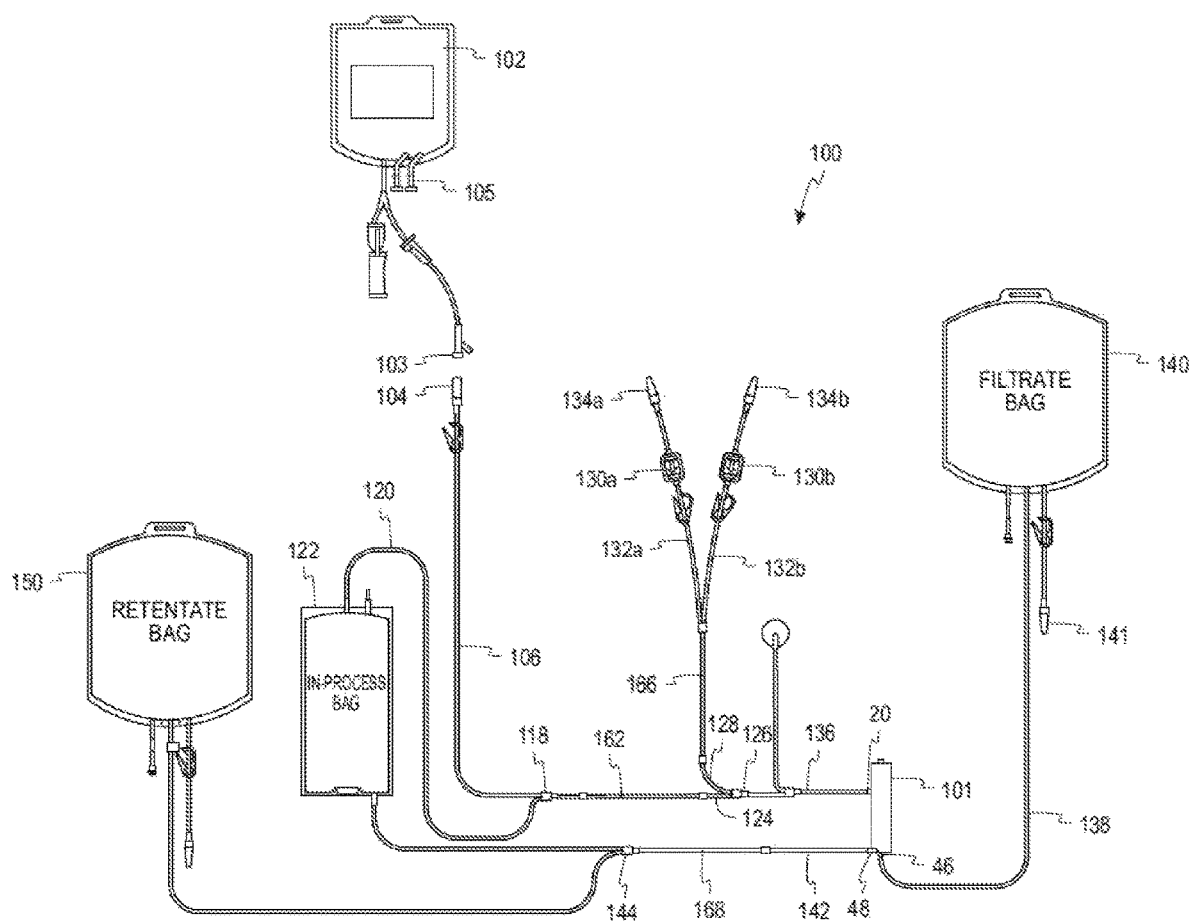
FIG. 3 is a schematic view of one embodiment of a disposable fluid circuit useful in the systems and methods described herein.

Turning now to FIG. 3, the systems described herein include at least one disposable fluid circuit 100 for use in the processing of biological fluid. While the circuits described herein may be used as stand-alone circuits, more preferably, at least two or more disposable fluid circuits are used in combination and in series for the separation, washing, volume reduction and/or other processing of a biological fluid. Circuit 100 may include an integrated separation device, such as, but not limited to, the spinning membrane 101 described above. Circuit 100 may also include waste container 140, product container 150, and in-process container 122. Disposable fluid circuits of the type described below may further include sampling assemblies (not shown) for collecting samples of source biological fluid, "final" product, or other intermediate products obtained during the biological fluid processing.

As will be seen in the Figures and described in detail below, the disposable fluid processing circuits include tubing that defines flow paths throughout the circuits, as well as access sites for sterile or other connection to containers of processing solutions, such as wash solutions, treating agents, or sources of biological fluid. As shown in FIG. 3, the tubing of circuit 100 includes spaced tubing segments identified by reference numerals 162, 166, 168. The tubing segments are provided for mating engagement with the peristaltic pumps 202, 204, 206 of the reusable hardware apparatus 200 discussed below. The containers and the plastic tubing are made of conventional medical grade plastic that can be sterilized by sterilization techniques commonly used in the medical field such as, but not limited to, radiation or autoclaving. Plastic materials useful in the manufacture of containers and of the tubing in the circuits disclosed herein include plasticized poly(vinyl chloride). Other useful materials include acrylics. In addition, certain polyolefins may also be used.

As will be apparent from the disclosure herein, source containers may be attached in sterile fashion to the circuit 100. Source containers 102 for connection to one disposable circuit may be the product containers 150 of another circuit used in an earlier step of the overall method of processing. Alternatively, the contents of a product container 150 may be further processed or separated and then transferred in sterile fashion to the source container 102 of a later-in-series fluid circuit.

The biological cell suspension to be washed or otherwise treated is typically provided in a source container 102, shown in FIG. 3 as (initially) not connected to the disposable set. As noted above, source container 102 may be attached (in sterile fashion) at the time of use. Source container 102 has one or more access sites 103, 105, one of which may be adapted for (sterile) connection to fluid circuit 100 at docking site 104. Preferably, source containers may be attached in a sterile manner by employing sterile docking devices, such as the BioWelder, available from Sartorius AG, or the SCD IIB Tubing Welder, available from Terumo Medical Corporation. A second access port 105 may also be provided for extracting fluid from the source container 102.

As further shown in FIG. 3, tubing segment 106 extends from docking site 104 and is connected to further downstream branched-connector 118. Branched-connector 118 communicates with tubing 106 and tubing 120, which provides a fluid flow path from "in-process" container 122, described in detail below. Tubing segment 124 extends from branched-connector 118 and is joined to a port of further downstream branched-connector 126. A separate flow path defined by tubing 128 is also connected to a port of branched-connector 126.

In accordance with the fluid circuit of FIG. 3, one or more containers of wash or other processing/treating solution may be attached (or pre-attached) to set 100. As shown in FIG. 3, tubings 132a, 132b (defining a flow path) preferably include and terminate in an access site such as spike connectors 134a, 134b. Access sites 134a, 134b are provided to establish flow communication with containers 135a, 135b (shown in FIG. 1) of a wash fluid, such as saline or other solution. Tubings 132a, 132b may include in-line sterile barrier filters 130a, 130b for filtering any particulate from a fluid before it enters the flow path leading to second branched-connector 126 and, ultimately separator 101. In one embodiment, the sterile barrier filters 130a, 130b may be 0.2 µm filters. The wash medium or fluid flows from the wash fluid source through tubing segments 132a, 132b where it is filtered by the sterile barrier filters 130a, 130b described above, and then passes through tubing 128 to the input of the branched-connector 126 described above.

Tubing segment 136 defines a flow path connected at one end to branched-connector 126 and to an inlet port 20 of the separator 101. Preferably, in accordance with the present disclosure, separation device 101 is a spinning membrane separator of the type described in U.S. Pat. Nos. 5,194,145 and 5,053,121, which are incorporated by reference, U.S. Provisional Patent Application Ser. No. 61/451,903 and PCT/US2012/028522, also previously incorporated herein by reference.

As shown in FIG. 3 (and described in detail in connection with FIG. 5), the spinning membrane separator 101 has at least two outlet ports. Outlet 46 of separator 101 receives the waste from the wash (i.e., the diluted suspension medium) and is connected to tubing 138, which defines a flow path to waste product container 140. The waste product container 140 includes a further connection port 141 for sampling or withdrawing the waste from within the product container.

Separation device 101 preferably includes a second outlet 48 that is connected to tubing segment 142 for directing the desired biological cell/fluid product to the in-process container(s) 122 or the product container 150. To permit this, the other end of tubing segment 142 is connected to branched-connector 144, which branches into and defines a flow path to one or more in-process containers 122 and a flow path to a "final" product container 150. The product container 150 may also include a sampling assembly (not shown).

Figure 4:
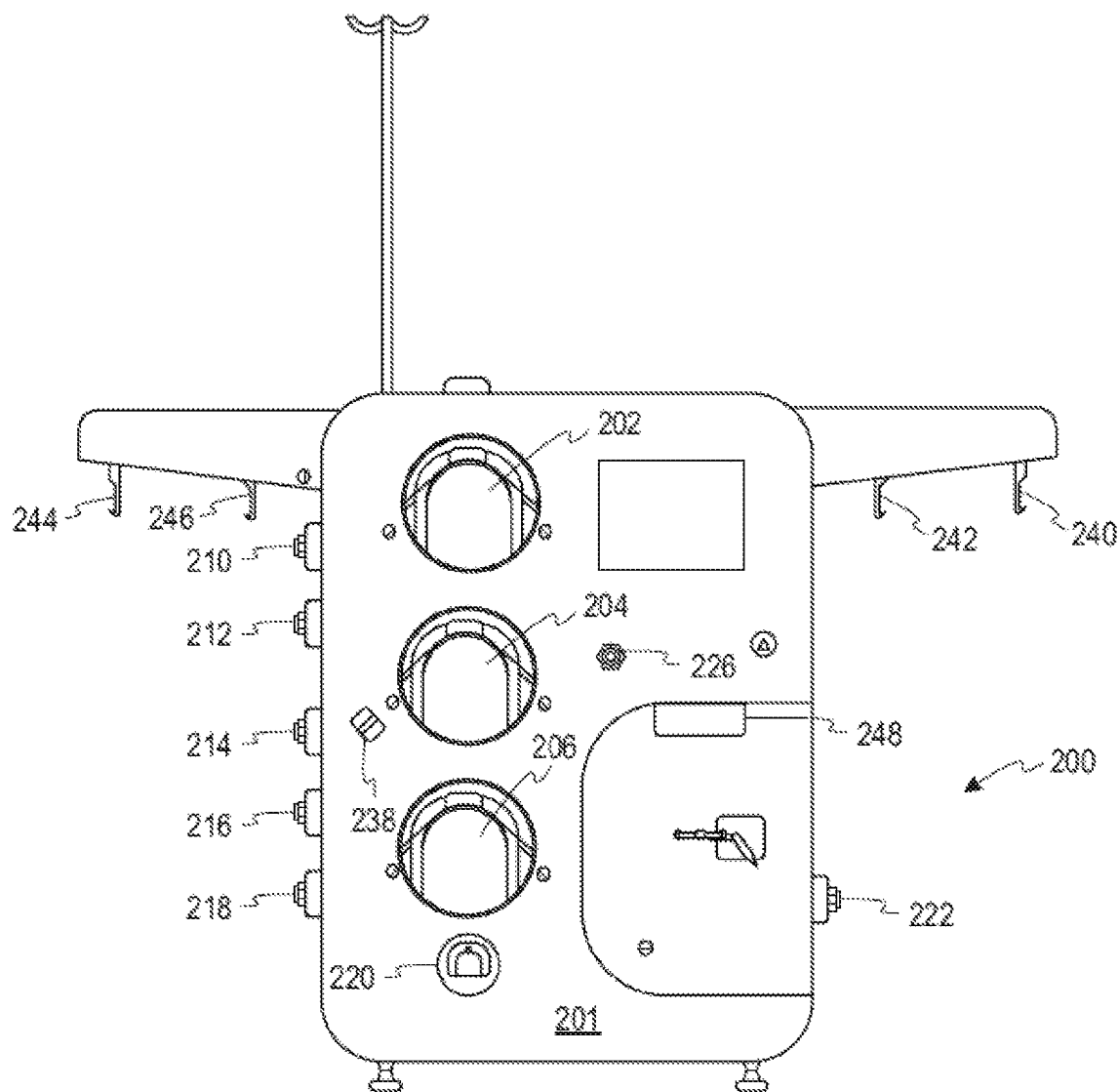
FIG. 4 is a frontal view of the reusable cell processing apparatus.

FIG. 4 shows the front panel 201 of reusable hardware processing apparatus 200, also referred to herein as "hardware". Apparatus 200 may be of compact size suitable for placement on a table top of a lab bench and adapted for easy transport. Alternatively, apparatus 200 may be supported by a pedestal that can be wheeled to its desired location. In any event, as shown in FIG. 4, apparatus 200 includes a plurality of peristaltic pumps such as pumps 202, 204 and 206 on front panel 201. Pump segments of the disposable fluid circuit (described above) are selectively associated with peristaltic pumps 202, 204, and 206. The peristaltic pumps articulate with the fluid set of FIG. 3 at the pump segments identified by reference numerals 162, 166, 168 and advance the cell suspension or other fluid within the disposable set, as will be understood by those of skill in the art. Apparatus 200 also includes clamps 210, 212, 214, 216, 218, 220 and 222. The clamps are used to control the flow of the cell suspension through different segments of the disposable set, as described above.

Apparatus 200 also includes several sensors to measure various conditions. The output of the sensors is utilized by device 200 to operate one or more wash or processing cycles. One or more pressure transducer sensor(s) 226 may be provided on apparatus 200 and may be associated with a disposable set 100 at certain points to monitor the pressure during a procedure. Pressure transducer 226 may be integrated into an in-line pressure monitoring site (at, for example, tubing segment 136), to monitor pressure inside separator 101. Air detector sensor 238 may also be associated with the disposable set 100, as necessary. Air detector 238 is optional and may be provided to detect the location of fluid/air interfaces.

Apparatus 200 includes weight scales 240, 242, 244, and 246 from which the final product container 150, waste container 140, the source container 102 and the in-process container 122, respectively, may depend and be weighed. The weights of the bags are monitored by weight sensors and recorded during a washing or other procedure. From measurements of the weight sensors, the device determines whether each container is empty, partially full, or full and controls the components of apparatus 200, such as the peristaltic pumps 202, 204 and 206 and clamps 210, 212, 214, 216, 218, 220 and 222.

Apparatus 200 includes at least one drive unit or "spinner" 248, which causes the indirect driving of the spinning membrane separator 101. Spinner 248 may consist of a drive motor connected and operated by apparatus 200, coupled to turn an annular magnetic drive member including at least a pair of permanent magnets. As the annular drive member is rotated, magnetic attraction between corresponding magnets within the housing of the spinning membrane separator cause the spinner within the housing of the spinning membrane separator to rotate.

Figure 5:
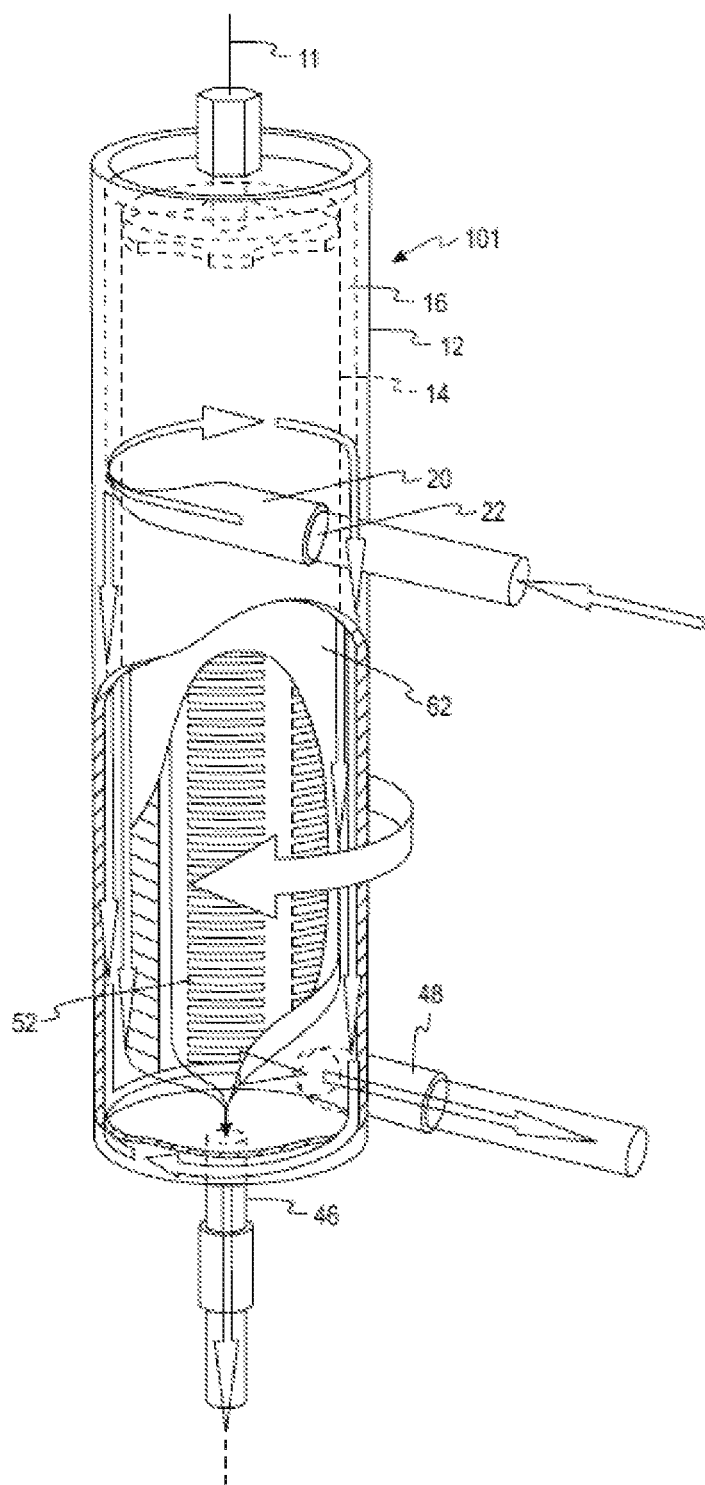
FIG. 5 is a perspective view of a separation/washing device using a spinning membrane.

Turning to FIG. 5, a spinning membrane separation device, generally designated 101, is shown. Such a device 101 forms part of the disposable circuit 100.

Device 101 includes a generally cylindrical housing 12, mounted concentrically about a longitudinal vertical central axis. An internal member 14 is mounted concentric with the central axis 11. Housing 12 and internal member 14 are relatively rotatable. In the preferred embodiment, as illustrated, housing 12 is stationary and internal member 14 is a rotating spinner that is rotatable concentrically within cylindrical housing 12, as shown by the thick arrow in FIG. 5. The boundaries of the flow path are generally defined by gap 16 between the interior surface of housing 12 and the exterior surface of rotary spinner 14. The spacing between the housing and the spinner is sometimes referred to as the shear gap. The shear gap may be approximately 0.02-0.06 inches (0.05-0.15 cm) and may be of a uniform dimension along axis 11, for example, where the axis of the spinner and housing are coincident. The shear gap may also vary circumferentially for example, where the axis of the housing and spinner are offset.

The shear gap also may vary along the axial direction, for example preferably an increasing gap width in the direction. Such a gap width may range from about 0.02 to about 0.075 inches (0.05-0.19 cm). The gap width could be varied by varying the outer diameter of the rotor and/or the inner diameter of the facing housing surface. The gap width could change linearly or stepwise or in some other manner as may be desired. In any event, the width dimension of the gap is preferably selected so that at the desired relative rotational speed, Taylor-Couette flow, such as Taylor vortices, are created in the gap.

Biological fluid is fed from an inlet conduit 20 through an inlet orifice 22, which directs the fluid into the fluid flow entrance region in a path tangential to the circumference about the upper end of the spinner 14. At the bottom end of the cylindrical housing 12, the housing inner wall includes an exit orifice 48.

Cylindrical housing 12 is completed by a bottom end housing terminating in an outlet orifice 46 concentric with the central axis.

In the illustrated embodiment, the surface of the rotary spinner 14 is at least partially, and is preferably substantially or entirely, covered by a cylindrical porous membrane 62. The membrane 62 may have a nominal pore size between 0.8 and 10 microns (μm), for example. Membranes may be fibrous mesh membranes, cast membranes, track-etched membranes or other types of membranes that will be known to those of skill in the art. For example, in one embodiment, the membrane may have a polyester mesh (substrate) with nylon particles solidified thereon, thereby creating a tortuous path through which only certain sized components will pass. In an embodiment, the nylon membrane may have a pore size of approximately 0.8 μm and a thickness of approximately 150 μm or greater. Membranes of this type will typically retain all cellular components (e.g., red blood cells, white blood cells) and certain formed blood components, e.g., platelets. In another embodiment, the membrane may be made of a thin (approximately 10 μm thick) sheet of unsupported polycarbonate, for example, with a pore size of approximately 4.0 μm. In this embodiment, pores (holes) may be cylindrical and larger than those described above. The pores may be sized to allow small formed components (e.g., platelets, microparticles, etc.) to pass, while the desired cells (e.g., white blood cells and larger red blood cells) are collected.

Having thus described the processor, including disposable circuit 100 and reusable hardware 200, reference is made to FIG. 2 to discuss additional details of the control unit or controller 300. As mentioned above, the controller 300 may include a microprocessor 304 (which, in fact may include multiple physical and/or virtual processors). According to other embodiments, the controller 300 may include one or more electrical circuits designed to carry out the actions described herein. In fact, the controller 300 may include a microprocessor and other circuits or circuitry. In addition, the controller 300 may include one or more memories 306. The instructions by which the microprocessor 304 is programmed may be stored on the memory 306 associated with the microprocessor 304, which memory/memories 306 may include one or more tangible non-transitory computer readable memories, having computer executable instructions stored thereon, which when executed by the microprocessor 304, may cause the microprocessors 304 to carry out one or more actions as described below.

As is also illustrated in FIG. 2, the controller 300 may be coupled to one or more of the structures described above, for example to receive information (e.g., in the form of signals) from these structures or to provide commands (e.g., in the form of signals) to these structures to control the operation of the structures. As illustrated, the controller 300 may be coupled to the scales 240, 242, 244, 246, the sensors 226, 238 and the at least one input 302 to receive information from those devices. Additionally, the controller 300 may be coupled to the pumps 202, 204, 206, the clamps 210, 212, 214, 216, 218, 220, 222, and the drive 248 to provide commands to those devices to control their operation. It may also be possible that the controller 300 receives information from and provides commands to a given structure, such as one of the structures already mentioned. The controller 300 may be directly electrically connected to these structures to be coupled to them, or the controller 300 may be directly connected to other intermediate equipment that is directly connected to these structures to be coupled to them.

The at least one input 302 may include a number of different devices according to the embodiments described herein. For example, the input 302 could include a keyboard or keypad by which a user may provide information and/or instructions to the controller 300. Alternatively, the input 302 may be a touch screen, such as may be used in conjunction with a video display 308 that is disposed on the front panel 201 of the device 200, the video display 308 also being coupled to the controller 300. The input could also include a reader or scanner, such as a barcode reader or scanner or an RFID reader. The assembly of the input/touch screen 302 and video display 308 may be one of the afore-mentioned structures to which the controller 300 is coupled from which the controller 300 receives information and to which the controller 300 provides commands. According to still other embodiments, the input 302 may be in the form of computer equipment that permits the cell processing system including the controller 300 to communicate (whether via wires, cables, etc. or wirelessly) with other cell processing systems over a local network, or with other cell processing systems or other computer equipment (e.g., a server) over local networks, wide area networks, or the Internet. According to such an embodiment, the input may include an internal transmitter/receiver device.

Having discussed the structure of embodiments of the cell processing system disclosed herein, the operation of the cell processing system is now discussed. In this regard, reference is made to U.S. Patent Application Pub. No. US 2013/0092630, the contents of which are incorporated herein by reference, which document discloses methods and systems for washing biological cells using a reusable hardware apparatus and disposable fluid circuit including a spinning membrane separator which may be generally applicable to the cell processing system described herein. The methods disclosed in this document involve the processing of biological cells, such as mononuclear cells for subsequent therapeutic administration.

In general terms, the operator may first activate (e.g., switch on) apparatus 200, at which point the apparatus 200 conducts self-calibration checks, including the checking of the peristaltic pumps 202, 204, 206, clamps 210, 212, 214, 216, 218, 220, 222, and sensors 226, 238. Apparatus 200 may then prompt the user to enter or modify process parameters using the input 302, including by way of example and not by way of limitation the amount of cell suspension to be processed, the number of cycles to take place, etc. The apparatus 200 may then prompt the operator to mount the disposable set 100, after which apparatus 200 automatically checks to determine whether the disposable set 100 is properly installed. Once the set 100 is properly installed, the controller 300 prompts the operator to connect the biological fluid (e.g., 102 of FIG. 3) via a spike connector or sterile connection (e.g., 103, 104 of FIG. 3) and the wash medium (e.g., 135a, 135b of FIG. 3) via a spike connector (e.g., 134a, 134b of FIG. 3). In one embodiment, the biological fluid/cells may be apheresis-collected mononuclear cells, and the wash medium may be a saline solution.

Once the operator confirms that the solutions are connected, the controller 300 primes the disposable set 100. In the embodiment discussed above, the set 100 may be primed with saline, although other bio-compatible aqueous solutions may also be used. The controller 300 then commences processing the biological fluid/cells. The biological fluid/cells is/are transferred from source container (e.g., 102 of FIG. 3) through the set to the spinning membrane separator 101 via the operation of one or more peristaltic pumps 202, 204 and 206. In a similar fashion, the wash medium is delivered from its container (e.g., 135a, 135b of FIG. 3) through the set to the spinning membrane separator 101. The biological cells are collected in either an in-process bag (e.g., 122 of FIG. 3) for additional processing or in a product container (e.g., 150 of FIG. 3), while supernatant is separated and removed to waste container (e.g., 140 of FIG. 3). Once the processing is completed, the controller prompts the operator to sample, seal and remove the product container 150.

A specific embodiment of a method 400 of operating the apparatus 200 is provided in FIG. 6. According to this embodiment, the method 400 of operating the apparatus 200 includes several steps, which steps may be grouped or organized into one or more cycles. For example, reduction, rinse and dilution steps 404, 406, 408 may define a first cycle, reduction, rinse, and dilution steps 414, 415, 416, 418 may define an optional intermediate cycle (which cycle may be omitted, or the steps 414, 415, 416 and/or 418 may be repeated several times to define intermediate cycles—e.g., a 6-cycle procedure may involve the performance of some or all of steps 414-418 a total of 4 times), and reduction, rinse, and dilution steps 424, 426, 428 may define a final cycle. It will be recognized that an apparatus 200 need not perform every step illustrated in FIG. 6, but an apparatus 200 may operate as illustrated in FIG. 6 according to this disclosure.

Preliminary to the first cycle, the controller 300 may perform an evaluation of the process to be performed by the apparatus 200 at block 390. According to certain embodiments, the evaluation is conducted using a mathematical model of the processor, as explained in detail below. The inputs for the model may include the process, or procedure, parameters received from the operator, via the input 302, for example. In the alternative or in addition, the inputs for the model may include process parameters that are stored by the controller 300, for example in the memory 306. These stored inputs may be in the form of default inputs that are used unless inputs are received via the input 302.

According to some embodiments, the mathematical model may include equations representative of the fluid flows from and to the containers 102, 122, 140, 150, of the other fluid flows within the processor 100, 200, and of the operation of the separator 101. In fact, according to preferred embodiments, the mathematical model is representative of the operation of the processor 100, 200 as illustrated in FIG. 6, from a priming step at block 402 to a final dilution step at block 428. The model may also include steps not illustrated in FIG. 6, such as an incubation step post the final dilution step at block 428. According to such embodiments, the controller 300 evaluates the entire process, from priming to final dilution, before the method 400 continues to block 402.

The results of the preliminary process evaluation at block 390 may be provided, displayed or used by the controller in different ways. For example, the controller 300 may provide or display outputs calculated as a consequence of the evaluation of the entire mathematical model, or only portions thereof, to the operator at block 392. Such outputs may include the duration of the process (as a whole), the duration of the priming step, the final volume in the waste container, the final volume in the product container, and the volume required in the wash media containers. The outputs may be provided or displayed on the display unit 308, for example. In addition or in the alternative, the controller 300 may limit or prevent the operation of the processor 100, 200 according to the process at block 394 if, for example, the process would cause the processor 100, 200 to exceed the abilities or performance characteristics of the processor 100, 200. The controller 300 may require at block 394 that an operator or an administrator (i.e., a user with greater control privileges than an operator) provide an override code (e.g., via the input 302) to allow the process to be performed. As an additional or alternative possibility, the controller 300 may limit or prevent operation of the processor 100, 200 at any point during the method 400 (e.g., at block 404) if measured in-process conditions differ from those calculated during the evaluation of the process. The measurements may involve signals received by the controller 300 from one or more of the scales 240, 242, 244, 246 mentioned above. The interruption of the process may be overridden by an operator or administrator using an override code (e.g., received by the controller 300 via the input 302) as mentioned above relative to the action at block 394.

Following this pre-process evaluation, the controller 300 may cause the apparatus 200 to perform the step of priming the set 100 at block 402. According to this step, wash media from the wash media containers 135a, 135b is transferred to the disposable set 100. Wash media may also be transferred to the source container 102. In fact, a small amount of wash media may be transferred to each of the other containers 102, 122, 140, 150 to ensure that the containers are connected 102, 122, 140, 150. To this end, the controller 300 may cause clamps 214, 216, 218, 220, 222 to open to permit the transfer of fluid to the containers 102, 122, 140, 150.

Once the priming is complete at block 402, the method 400 continues to block 404, where the controller 300 causes the apparatus 200 to perform the first cycle reduction step. According to this step, the controller 300 causes the biological fluid from the source container 102 and wash media from the wash media container(s) 135a, 135b to be transferred to the separator 101. For example, the controller 300 may open clamps 214, 212 (and/or 210) and operate pumps 204, 202 to transfer the fluids from the containers 102, 135a (and/or 135b) to the separator 101. The separator 101 (in conjunction with operation of the drive 248 by controller 300) produces two streams: a first, or retentate, stream that is directed into the in-process container 122, and a second, or filtrate, stream that is directed into the waste container 140. For example, the controller 300 may open clamp 218 and operate pump 206 to cause flow into the in-process container 122 (clamp 220 being closed), and may open clamp 222 to permit flow into the container 140. After the step of block 404 is complete, the controller 300 causes wash media to be passed through the set (i.e., the set is rinsed) and the media is added to the in-process bag 122 at block 406. This may be achieved, for example, by closing clamps 214, 222, while leaving clamps 212 (and/or 210), 218 open and operating pumps 202, 206. After block 406, the method 400 proceeds to block 408, where the controller 300 causes additional wash media to be added to the in-process bag 122. When block 408 is complete, the method 400 passes from the first cycle to the intermediate cycle.

At optional block 414, the controller 300 may cause the apparatus 200 to further reduce the fluid in the in-process bag 122 by transferring the fluid to the separator 101 without additional dilution, and passing the supernatant to the waste container 140 while the cells are returned to the in-process bag 122. For example, the controller 300 opens clamps 216, 218, 222 and operates pumps 204, 206 and drive 248. The controller 300 may continue to cause the apparatus 200 to perform this step until certain user-defined limits have been satisfied. It is also possible that the controller 300 may skip this optional step entirely while operating according to the method 400, and proceed instead to step 415.

At optional block 415, the controller 300 may cause the apparatus 200 to operate such that the feed into the separator 101 is maintained at a constant packed cell volume (PCV). Because cells are being processed from the in-process container 122, concentrated, and then directed back to the in-process container 122, the PCV of the in-process container 122 would continuously increase. To limit or prevent the continuous increase, the controller 300 causes the apparatus 200 is add wash media at increasing rates. As such, the controller may open clamp 212 (and/or 210) and clamps 216, 218, 222 while operating pumps 202, 204, 206 and drive 248, for example.

Once block 415 is complete, the controller 300 may cause the apparatus to perform a rinse of the set at block 416 and to add wash media to the in-process bag 122 at block 418. When block 418 is complete, the method 400 passes from the intermediate cycle to the final cycle.

The final cycle begins with block 424, where the controller 300 causes the biological fluid from the in-process container 122 and wash media from the wash media containers 135a, 135b to be transferred to the separator 101. For example, the controller 300 may open clamps 216, 212 (and/or 210) and operate pumps 204, 202 to transfer the fluids from the containers 102, 135a (and/or 135b) to the separator 101. Again, the separator 101 produces two streams: a first, or retentate, stream that is directed into the retentate, or product, container 150 (instead of the in-process container 122), and a second, or filtrate, stream that is directed into the waste container 140. For example, the controller 300 may open clamp 220 and operate pump 206 to cause flow into the product container 150, and may open clamp 222 to permit flow into the container 140. After the step of block 424 is complete, the controller 300 causes wash media to be passed through the set (i.e., the set is rinsed) and the media is added to the product bag 150 at block 426. This may be achieved, for example, by closing clamps 216, 222, while leaving clamps 212 (and/or 210), 220 open and operating pumps 202, 206. After the block 426, the method 400 proceeds to block 428, where the controller 300 causes wash media to be added to the product bag 150. When block 428 is complete, the method 400 may continue with other steps, such as incubation, as are desired before the product bag 150 is sampled, sealed and removed from the apparatus 200.

Having discussed the method 400, a method 500 of performing the preliminary or pre-process evaluation of the process (i.e., 390 in FIG. 6) is illustrated in FIG. 7. The method 500 begins at block 502, with receipt by the controller 300 of the input configuration, i.e., the process parameters required for the processor 100, 200 to perform the process or procedure. The controller 300 may receive the input configuration via the input 302, as mentioned above.

As also mentioned above, the controller 300 may receive the process parameters from the memory 306 associated with the controller 300. In fact, certain process parameters may be initialized to a default value according to values stored in the memory 306, some or all of which may be modified by the user (e.g., operator or administrator) via the input 302, for example.

The method 500 may continue at block 504, where the input configuration received at block 502 is evaluated for completeness. For example, the controller 300 may verify that a value has been received for each process parameter in the input configuration. Further, the controller 300 may verify that the values received fall within a preset range for such parameters. The controller 300 may perform other verifications as well. If the controller 300 determines that one or more of the process parameters are missing from the input configuration (or fail to fall within the required range, for example), the process 500 returns to block 502. Otherwise, the method 500 continues to block 506.

At block 506, the controller 300 performs calculations representative of the priming of the set 100 (see, block 402 of FIG. 6). For example, information regarding the number of priming actions and the identity of the source of the priming fluid (and whether that source is also used as the source for the wash media for the entire procedure) may be received. Based on this information in combination with information relating to the volume of the tubing, of the separator, etc., the controller 300 may calculate the volumes and volume fractions expected to be present in the containers at the end of the priming step, as well as the time required to perform this part or portion of the procedure. The method then continues to block 508.

At block 508, the controller 300 performs the calculations representative of the separation of the biological fluid into two streams. This is representative of the separation occurring at block 404 of FIG. 6, for example. As part of the calculations, the controller sets flow rates for each of a plurality of volumes (each volume representing one of the containers and the separator). The controller 300 also sets the initial volumes for certain of the containers and initial volume fractions. Based on this information, the controller 300 then calculates the volumes and volume fractions expected to be present in the containers at the end of the separation step, as well as other information, such as the time required to complete this part of the process and/or the time required to complete the process to this point.

In doing so, the controller 300 at block 508 uses the final volumes and final volume fractions from the preceding step as the initial volumes and initial volume fractions for this step. According to certain embodiments, including the illustrated embodiment, the controller 300 generally uses the final volumes and final volume fractions from the preceding step as the initial volumes and initial volume fractions for the following step. As a consequence, to calculate the outputs discussed above, the controller 300 first carries out the calculations for every step of the process or procedure, because each succeeding step builds on each prior step.

A comparison may be performed between certain calculated in-process conditions and controls for those conditions at block 510. While the comparison is illustrated as a separate block 510, the comparisons may be made while the calculations that occur as part of block 508 are performed. The comparison may involve determining if the calculated condition matches a control. In this regard, "matching" may include being identical to the control value, or within a certain range of control values. "Matching" may also include satisfying a particular relationship to the control value, such as exceeding or not exceeding the control value. If the comparison is not satisfied (i.e., the calculated value does not match the control value), then a warning or error indication may be provided to the operator, via the video display 308, for example.

At blocks 512, 514, the controller 300 performs calculations representative of the rinse and dilution actions performed, for example, at blocks 406, 408 in FIG. 6. As part of this calculation, the controller 300 receives information as to which wash media volume/container (e.g., container 135a or 135b) will provide the wash media for the rinse and/or dilution steps. The controller 300 uses the volumes and volume fractions from the previous step as the initial values, and then calculates the final volumes and volume fractions. The controller 300 may also calculate the procedure time for this part (or step) and/or to the completion of the step.

The method 500 continues at block 516, 520, where calculations are performed representative of the actions performed at blocks 414, 415 in FIG. 6. At block 520, because the wash media will be added at increasing rates during the corresponding step of the process 400, the controller 300 approaches the calculation of the rates, volumes and volume fractions as a series of calculations performed over an iterative timescale. Alternatively, if either corresponding step of the process (i.e., 414, 415) is omitted, then the final volumes and volume fractions at blocks 516, 520 are set equal to the initial volumes and volume fractions, and the time for the step is set equal to zero.

As was the case relative to the calculations performed at block 508, the method 500 includes comparisons of some of the calculated conditions with controls for those conditions at blocks 518, 522 (similar to block 510, above). As was also the case above, while the comparisons are illustrated as separate blocks 518, 522, the comparisons may occur during the calculations at blocks 516, 520. The method then continues at blocks 524, 526 with calculations representative of the rinse and dilution steps at blocks 416, 418 in FIG. 6. The calculations performed here are similar to those performed at blocks 512, 514.

In the same manner that the foregoing calculations and comparisons at blocks 516, 518, 520, 522, 524, 526 may be omitted if some or all of the steps of the intermediate cycle (i.e., blocks 414, 415, 416, 418) are omitted, the calculations and comparisons at blocks 516, 518, 520, 522, 524, 526 may be repeated if some or all of the steps of the intermediate cycle are repeated to define a process of more than three cycles.

The method 500 concludes with calculations at blocks 528, 532, 534 representative of the actions at blocks 424, 426, 418 in FIG. 6. The method also performs a comparison of calculated conditions and controls at block 530, similar to the comparison described above at block 510. The calculations performed at blocks 528, 532, 534 and the comparisons performed at block 530 are similar to those described above relative to blocks 508, 512, 514 and 510, and as such will not be repeated. The method 500 then concludes, with the subsequent use of the outputs and/or in-process conditions at blocks 392, 394 of FIG. 6 as discussed above.

The systems and methods described herein may be effective, for example, in the washing of cells such as red blood cells and/or white blood cells. In one example of red cell washing, stored red blood cells may be washed to remove accumulated free hemoglobin, spent storage solution, or extracellular components. The washing solution may be sterile docked or otherwise included in the closed system of the disposable processing set of the type described above. The treated cells may then be washed with the washing solution such as saline, Adsol or E-Sol (the latter of which are red blood cell storage solutions and generally comprise dextrose, mannitol and a buffer) to reconstitute the red blood cells for subsequent storage and transfusion.

The initial cell feed may be diluted by combining the feed from container 102 with diluent (wash solution) from container 135 at branched connector 126. In one embodiment, diluent from container 135 may initially be drawn into separator, followed by the cell feed drawn from container 102 and combined with the diluent, as described.

Thus, an improved method and system have been disclosed for the processing of biological cells. The description provided above is intended for illustrative purposes only and is not intended to limit the scope of the invention to any specific method, system, or apparatus, or device described herein except as may be explicitly delineated above.

In conclusion, according to one aspect, a cell processing system includes a processor connectable to a source container filled with a biological fluid, the processor including a separator configured to separate the biological fluid from the source container into at least two streams according to a process including at least one process parameter, and a controller coupled to the processor and an input. The controller is configured to receive the at least one process parameter via the input, to calculate at least one output based on the at least one process parameter, and to provide the at least one calculated output to an operator prior to causing the processor to operate according to the process.

The at least one calculated output includes one or more of a time to complete the process, or a part thereof, a volume of wash media consumed, a volume of waste fluid generated, and a volume of a residual remaining in a product. Further, the controller may be configured to calculate the at least output based on the at least one process parameter and each step of the process.

According to another aspect, a cell processing system includes a processor connectable to a source container filled with a biological fluid, the processor including a separator configured to separate the biological fluid from the source container into at least two streams according to a process including at least one process parameter, and a controller coupled to the processor and an input. The controller is configured to receive the at least one process parameter via the input, to calculate at least one in-process condition based on the at least one process parameter, to compare the at least one calculated in-process condition with at least one in-process condition control, and to provide an error indication to an operator if the at least one calculated in-process condition does not match the at least one in-process condition control prior to causing the processor to operate according to the process.

According to such an aspect, the controller may be configured to calculate a plurality of in-process conditions corresponding to each step that defines the process, to compare a set of the plurality of calculated in-process conditions with a set of in-process condition controls, and to provide an error indication to the operator if any element of the set of calculated in-process conditions does not match a corresponding element of the set of in-process condition controls.

According to a still further aspect, a cell processing system includes a processor connectable to a source container filled with a biological fluid, the processor including a separator configured to separate the biological fluid from the source container into at least two streams according to a process including at least one process parameter, and a controller coupled to the processor and an input. The controller is configured to receive at least one process parameter via the input, to calculate at least one in-process condition based on the at least one process parameter prior to causing the processor to operate according to the process, to subsequently cause the processor to operate according to the process, to measure at least one in-process condition during operation of the processor, to compare the at least one calculated in-process condition with at least one measured in-process condition, and to provide an error indication to an operator if the at least one measured in-process condition does not match the at least one calculated in-process condition.

According to such an aspect, the controller may be configured to calculate a plurality of in-process conditions corresponding to each step that defines the process prior to causing the processor to operate according to the process, to compare a set of the plurality of calculated in-process conditions with a set of measured in-process conditions, and to provide an error indication to the operator if any element of the set of measured in-process conditions does not match a corresponding element of the set of calculated in-process conditions.

According to any of the foregoing aspects, the processor may include a disposable fluid circuit and reusable hardware. In fact, the disposable fluid circuit may include a spinning membrane separation device, at least one container, and tubing connecting the spinning membrane and the one or more containers.

According to yet another aspect, a method for evaluating a process is provided, the process to be performed using a processor connectable to a source container filled with a biological fluid, the processor including a separator configured to separate the biological fluid from the source container into at least two streams. The method includes receiving the at least one process parameter to be used during the process, calculating at least one output based on the at least one process parameter, and providing the at least one calculated output to an operator prior to operating the processor according to the process.

According to such an aspect, the at least one calculated output may be one of a time to complete the process, or a part thereof, a volume of wash media consumed, a volume of waste fluid generated, and a volume of a residual remaining in a product. The step of calculating at least one output may include calculating the at least one output based on the at least one process parameter and each step of the process.

According to a further aspect, a method for evaluating a process is provided, the process to be performed using a processor connectable to a source container filled with a biological fluid, the processor including a separator configured to separate the biological fluid from the source container into at least two streams. The method includes receiving at least one process parameter to be used during the process, calculating at least one in-process condition based on the at least one process parameter, comparing the at least one calculated in-process condition with at least one in-process condition control, and providing an error indication to an operator if the at least one calculated in-process condition does not match the at least one in-process condition control prior to operating the processor according to the process.

The method may further include calculating a plurality of in-process conditions corresponding to each step that defines the process, comparing a set of the plurality of calculated in-process conditions with a set of in-process condition controls, and providing an error indication to the operator if any element of the set of calculated in-process conditions does not match a corresponding element of the set of in-process condition controls.

According to a still further aspect, a method for evaluating a process is provided, the process to be performed using a processor connectable to a source container filled with a biological fluid, the processor including a separator configured to separate the biological fluid from the source container into at least two streams. The method includes receiving at least one process parameter to be used during the process, calculating at least one in-process condition based on the at least one process parameter prior to operating the processor according to the process, causing subsequently the processor to operate according to the process, measuring at least one in-process condition during operation of the processor, comparing the at least one calculated in-process condition with at least one measured in-process condition, and providing an error indication to an operator if the at least one measured in-process condition does not match the at least one calculated in-process condition. Furthermore, the method according to this aspect may include calculating a plurality of in-process conditions corresponding to each step that defines the process prior to causing the processor to operate according to the process, comparing a set of the plurality of calculated in-process conditions with a set of measured in-process conditions, and providing an error indication to the operator if any element of the set of measured in-process conditions does not match a corresponding element of the set of calculated in-process conditions.

The invention claimed is:

1. A cell processing system comprising:
   a processor connectable to a source container filled with a biological fluid, the processor including a separator configured to separate the biological fluid from the source container into at least two streams according to a process including at least one process parameter; and
   a controller coupled to the processor and an input, the controller configured:
   to receive the at least one process parameter via the input;
   to calculate, using a mathematical model of the process that defines how the separator separates the biological fluid from the source container into the at least two streams, at least one output of the process based on the at least one process parameter and each step of the process step-by-step, the process comprising a plurality of steps with each following step depending on each preceding step;
   to provide the at least one calculated output of the process to an operator prior to causing the processor to operate according to the process to separate the biological fluid from the source container into the at least two streams.

2. The cell processing system according to claim 1, wherein the at least one calculated output comprises a time to complete the process, or a part thereof, a volume of wash media consumed in the process, a volume of waste fluid generated in the process, and a volume of a residual remaining in a product produced by the process.

3. The cell processing system according to claim 1, wherein the processor comprises a disposable fluid circuit and reusable hardware.

4. The cell processing system according to claim 3, wherein the disposable fluid circuit comprises a spinning membrane separation device, at least one container, and tubing connecting the spinning membrane and at least one container.

5. The cell processing system according to claim 1, wherein the controller is configured to calculate the at least one output of the process based on the at least one process parameter and a calculation of each step of the process, with the calculation of the each following step building on the each preceding step.

6. The cell processing system according to claim 5, wherein the controller is configured to calculate final volumes and final volume fractions for the each preceding step and to use the final volumes and the final volume fractions of the each preceding step as initial volumes and initial volume factions for the calculation of the each following step.

7. The cell processing system according to claim 5, wherein the mathematical model includes one or more optional steps, and the controller is configured to include or omit the one or more optional steps in calculating the at least one output of the process based on the at least one process parameter and the each step of the process.

8. A cell processing system comprising:
a processor connectable to a source container filled with a biological fluid, the processor including a separator configured to separate the biological fluid from the source container into at least two streams according to a process including at least one process parameter; and
a controller coupled to the processor and an input, the controller configured:
to receive the at least one process parameter via the input;
to calculate, using a mathematical model of the process that defines how the separator separates the biological fluid from the source container into the at least two streams, at least one output of the process based on the at least one process parameter and each step of the process step-by-step, the process comprising a plurality of steps with each following step depending on each preceding step, wherein calculating the at least one output of the process includes calculating at least one in-process condition based on the at least one process parameter;
to compare the at least one calculated in-process condition with at least one in-process condition control; and
to provide an error indication to an operator if the at least one calculated in-process condition does not match the at least one in-process condition control prior to causing the processor to operate according to the process to separate the biological fluid from the source container into the at least two streams.

9. The cell processing system according to claim 8, wherein the controller is configured:
to calculate a plurality of in-process conditions;
to compare a set of the plurality of calculated in-process conditions with a set of in-process condition controls; and
to provide an error indication to the operator if any element of the set of calculated in-process conditions does not match a corresponding element of the set of in-process condition controls.

10. The cell processing system according to claim 8, wherein the processor comprises a disposable fluid circuit and reusable hardware.

11. The cell processing system according to claim 10, wherein the disposable fluid circuit comprises a spinning membrane separation device, at least one container, and tubing connecting the spinning membrane and at least one container.

12. The cell processing system according to claim 8, wherein the controller is configured to calculate the at least one output of the process based on the at least one process parameter and a calculation of each step of the process, with the calculation of the each following step building on the each preceding step.

13. The cell processing system according to claim 12, wherein the controller is configured to calculate final volumes and final volume fractions for the each preceding step and to use the final volumes and the final volume fractions of the each preceding step as initial volumes and initial volume factions for the calculation of the each following step.

14. The cell processing system according to claim 12, wherein the mathematical model includes one or more optional steps, and the controller is configured to include or omit the one or more optional steps in calculating the at least one output of the process based on the at least one process parameter and the each step of the process.

15. A cell processing system comprising:
a processor connectable to a source container filled with a biological fluid, the processor including a separator configured to separate the biological fluid from the source container into at least two streams according to a process including at least one process parameter; and
a controller coupled to the processor and an input, the controller configured:
to receive the at least one process parameter via the input;
to calculate, using a mathematical model of the process that defines how the separator separates the biological fluid from the source container into the at least two streams, at least one output of the process based on the at least one process parameter and each step of the process step-by-step, the process comprising a plurality of steps with each following step depending on each preceding step, wherein calculating the at least one output of the process includes calculating at least one in-process condition based on the at least one process parameter prior to causing the processor to operate according to the process to separate the biological fluid from the source container into the at least two streams;
to subsequently cause the processor to operate according to the process;
to measure at least one in-process condition during operation of the processor;
to compare the at least one calculated in-process condition with at least one measured in-process condition; and
to provide an error indication to an operator if the at least one measured in-process condition does not match the at least one calculated in-process condition.

16. The cell processing system according to claim 15, wherein the controller is configured:
to calculate a plurality of in-process conditions prior to causing the processor to operate according to the process;
to compare a set of the plurality of calculated in-process conditions with a set of measured in-process conditions; and
to provide an error indication to the operator if any element of the set of measured in-process conditions does not match a corresponding element of the set of calculated in-process conditions.

17. The cell processing system according to claim 15, wherein the processor comprises a disposable fluid circuit and reusable hardware.

18. The cell processing system according to claim 17, wherein the disposable fluid circuit comprises a spinning membrane separation device, at least one container, and tubing connecting the spinning membrane and at least one container.

19. The cell processing system according to claim 15, wherein the controller is configured to calculate the at least one output of the process based on the at least one process parameter and a calculation of each step of the process, with the calculation of the each following step building on the each preceding step.

20. The cell processing system according to claim 19, wherein the controller is configured to calculate final volumes and final volume fractions for the each preceding step and to use the final volumes and the final volume fractions of the each preceding step as initial volumes and initial volume factions for the calculation of the each following step.

21. The cell processing system according to claim 19, wherein the mathematical model includes one or more optional steps, and the controller is configured to include or omit the one or more optional steps in calculating the at least one output of the process based on the at least one process parameter and the each step of the process.

* * * * *